(12) United States Patent
Zerbe et al.

(10) Patent No.: US 9,949,934 B1
(45) Date of Patent: Apr. 24, 2018

(54) DEVICE AND METHOD OF TREATING CONDITIONS ASSOCIATED WITH NEUROINFLAMMATION

(71) Applicant: Intelgenx Corp., Saint-Laurent (CA)

(72) Inventors: Horst G. Zerbe, Hudson (CA);
Rodolphe Obeid, St-Laurent (CA);
Justin W. Conway, Carignan (CA);
Nadine Paiement, St-Laurent (CA);
Ludwig Aigner, Freilassing (DE)

(73) Assignee: Intelgenx Corp., Saint-Laurent Quebec (CA)

( * ) Notice: Subject to any disclaimer, the term of this patent is extended or adjusted under 35 U.S.C. 154(b) by 0 days.

(21) Appl. No.: 15/299,054

(22) Filed: Oct. 20, 2016

(51) Int. Cl.
*A61K 9/70* (2006.01)
*A61K 31/4704* (2006.01)
*C07D 215/18* (2006.01)
*A61K 31/404* (2006.01)
*A61K 31/381* (2006.01)
*A61K 31/47* (2006.01)

(52) U.S. Cl.
CPC .......... *A61K 9/7007* (2013.01); *A61K 31/381* (2013.01); *A61K 31/404* (2013.01); *A61K 31/47* (2013.01)

(58) Field of Classification Search
None
See application file for complete search history.

(56) References Cited

U.S. PATENT DOCUMENTS

| | | |
|---|---|---|
| 8,575,194 B1 | 11/2013 | Schultz |
| 9,149,472 B2 | 10/2015 | Schultz |
| 2013/0039932 A1* | 2/2013 | Park ..................... A61K 9/0056 424/184.1 |
| 2013/0177605 A1* | 7/2013 | Asari ..................... A61K 47/02 424/400 |

FOREIGN PATENT DOCUMENTS

| | | | |
|---|---|---|---|
| EP | 0743064 A1 | 11/1996 | |
| WO | WO 9940898 A2 * | 8/1999 | ............. A61K 9/006 |

OTHER PUBLICATIONS

Rao (Raghavendra Rao N. G., et al., Development of mucoadhesive films for buccal administration of montelukast, International Journal of Pharmacy&Technology, Mar. 2010. vol. 2 Issue No. 1, pp. 1-15.*

* cited by examiner

*Primary Examiner* — H S Park
(74) *Attorney, Agent, or Firm* — Gunther J. Evanina; Butzel Long

(57) ABSTRACT

Disclosed is a device and method for treating a neurodegenerative disease or condition associated with neuroinflammation induced by a leukotriene. The device is a film unit dosage form having a film layer and a safe and effective amount of a leukotriene receptor antagonist or leukotriene synthesis inhibitor. The device is configured and formulated to achieve transmucosal and/or enteral delivery of the leukotriene receptor antagonist or leukotriene synthesis inhibitor. The method includes transmucosally and/or enterally delivering to an animal in need of treatment, a safe and effective amount of a leukotriene blocker capable of crossing the blood-brain barrier.

3 Claims, No Drawings

DEVICE AND METHOD OF TREATING CONDITIONS ASSOCIATED WITH NEUROINFLAMMATION

CROSS-REFERENCE TO RELATED APPLICATIONS

Not Applicable

FIELD OF THE DISCLOSURE

This disclosure concerns treatment of neurological conditions by administration of a leukotriene receptor antagonist or leukotriene synthesis inhibitor.

BACKGROUND OF THE DISCLOSURE

As the brain ages, it loses its ability to generate new cells, while existing cells lose functionality, including the ability to prevent inflammatory mediators in the blood from passing through the blood-brain barrier. At the same time the aged brain tends to produce higher levels of inflammatory agents such as leukotrienes, and loses some of its ability to counter the effects of inflammatory mediators, resulting in neuroinflammation and cognitive impairment. A major contributor to neuroinflammation are leukotrienes. There is evidence that leukotriene receptor antagonists, such as Montelukast sodium, have the potential to reduce neuroinflammation and restore brain cell function. Such treatments can be effective for treating various neurodegenerative diseases and conditions, including Huntington's disease, Parkinson's disease, loss of memory function, spinal cord and brain injuries, and stroke.

Montelukast sodium (MTL) is an orally active leukotriene receptor antagonist commonly used to treat patients suffering from chronic asthma as well as symptomatic relief of seasonal allergic rhinitis. During a normal respiratory inflammation response, the binding of cysteinyl leukotrienes to the leukotriene receptor induces inflammation within the respiratory pathway, generating asthmatic symptoms. MTL functions to suppress this inflammatory response by binding to the leukotriene receptor with high affinity and selectivity, thereby blocking the pathway leading to the physiological response for extended periods. Recently, neuroinflammation within the brain has been linked to age-related dementia and neurodegenerative diseases. MIL applied under these biological conditions has been shown to significantly reduce neuroinflammation, elevate hippocampal neurogenesis and improve learning and memory in old animals.

Presently, Montelukast sodium is marketed in a tablet form under the name of "Singulair®." One of the greatest challenges for using MTL in a tablet form is the inconsistent bioavailability. Although MTL is freely soluble in water, its solubility is reduced under acidic conditions normally found in the stomach. This has led to relatively slow and inconsistent absorption into the blood stream, with maximum concentrations occurring only after 2-4 hours, thereby limiting its use to chronic applications rather than for rapid acute treatment. Experimental studies indicate that the major obstacles limiting MTL absorption pertain to its solubility, the rate of dissolution from the tablet platform and transport across biological membranes.

U.S. Pat. Nos. 8,575,194 and 9,149,472 disclose methods of improving cognitive impairments by administering a single tablet or capsule that comprises an extended release (ER) component and an immediate release (IR) component in a single dosage unit. The method involves administering the dosage unit to provide an initial burst of IR API into the system, followed by the ER API over the course of 12 hours, thereby maintaining a constant effective plasma level. Disclosed embodiments include a tablet with an ER core and an IR shell or a capsule containing a mixture of ER and IR beads combined in a specific ratio to achieve the desired effect. In an alternative embodiment, the regimen in general consists of an initial high dose of 10 mg of MTL followed by 5 mg doses approximately every 2 hours afterwards over the course of 12 hours. The patents discuss plasma levels as being critical for achieving cognitive improvement. However, MTL can only exert its therapeutic effects if it crosses the blood-brain barrier (BBB) and accumulates in the cerebrospinal fluid (CSF) at sufficient concentration levels. Neither plasma nor CSF concentration levels of MTL are discussed in the patents.

SUMMARY OF THE DISCLOSURE

Disclosed is a film dosage form for delivering to the brain a safe and effective amount of an agent for reducing neuroinflammation. The film dosage form includes a biocompatible film layer having an active agent selected from leukotriene receptor antagonists, leukotriene synthesis inhibitors, and combinations of these agents. The film layer is configured for transmucosal and/or enteral delivery of the active agent.

The film layer can be configured for oral transmucosal and oral delivery of the active agent(s).

In certain embodiments, the active agent in the film dosage form is Montelukast sodium.

Also disclosed is a method of treating neurodegenerative diseases and conditions at least partially induced by leukotrienes, by administering to a person or other animal in need of treatment, a film dosage form including a film layer including an active agent selected from leukotriene receptor antagonists, leukotriene synthesis inhibitors and combinations of these agents. The film layer is configured for transmucosal and/or enteral delivery of the active agent.

These and other features, advantages and objects of the various embodiments will be better understood with reference to the following specification and claims.

DETAILED DESCRIPTION OF ILLUSTRATIVE EMBODIMENTS

In accordance with certain aspects of this disclosure methods for treating neurodegenerative diseases and conditions that are at least partially induced by leukotrienes are provided. These methods involve transmucosal and/or enteral delivery of at least one of a leukotriene receptor antagonist and a leukotriene synthesis inhibitor. Combinations of these agents may be employed. The active agent(s) is (are) incorporated into a film layer in an amount that is safe and effective to reduce leukotriene induced neuroinflammation in patients.

Neurodegenerative diseases that can be treated in accordance with this disclosure include, but are not limited to, loss of memory function (long term or short term), dementia, apathy, depression, fatigue (acute or chronic), cognitive losses, loss of focus, loss of libido, and disorientation. Specific disease conditions that can be treated with the disclosed methods include Huntington's disease, Parkinson's disease and Alzheimer's disease. Such treatments can also be effective for treating neurological diseases, neurodegenerative diseases, neuroinflammatory disorders, traumatic or posttraumatic disorders, vascular or more precisely, neurovascular disorders, hypoxic disorders, and postinfectious central nervous system disorders. The term "neurodegenerative disease" or "neurological disease" or "neuroinflammatory disorder" refers to any disease, disorder, or condition affecting the central or peripheral nervous system, including ADHD, AIDS-neurological complications, absence of the Septum Pellucidum, acquired epileptiform aphasia, acute disseminated encephalomyelitis, adrenoleukodystrophy, agenesis of the Corpus Callosum, agnosia, Aicardi Syndrome, Alexander Disease, Alpers' Disease, alternating hemiplegia, Alzheimer's Disease, amyotrophic lateral sclerosis (ALS), anencephaly, aneurysm, Angelman Syndrome, angiomatosis, anoxia, aphasia, apraxia, arachnoid cysts, arachnoiditis, Arnold-Chiari Malformation, arteriovenous malformation, aspartame, Asperger Syndrome, ataxia telangiectasia, ataxia, attention deficit-hyperactivity disorder, autism, autonomic dysfunction, back pain, Barth Syndrome, Batten Disease, Behcet's Disease, Bell's Palsy, benign essential blepharospasm, benign focal amyotrophy, benign intracranial hypertension, Bernhardt-Roth Syndrome, Binswanger's Disease, blepharospasm, Bloch-Sulzberger Syndrome, brachial plexus birth injuries, brachial plexus injuries, Bradbury-Eggleston Syndrome, brain aneurysm, brain injury, brain and spinal tumors, Brown-Sequard Syndrome, bulbospinal muscular atrophy, Canavan Disease, Carpal Tunnel Syndrome, causalgia, cavernomas, cavernous angioma, cavernous malformation, central cervical cord syndrome, central cord syndrome, central pain syndrome, cephalic disorders, cerebellar degeneration, cerebellar hypoplasia, cerebral aneurysm, cerebral arteriosclerosis, cerebral atrophy, cerebral beriberi, cerebral gigantism, cerebral hypoxia, cerebral palsy, cerebro-oculo-facio-skeletal syndrome, Charcot-Marie-Tooth Disorder, Chiari Malformation, chorea, choreoacanthocytosis, chronic inflammatory demyelinating polyneuropathy (CIDP), chronic orthostatic intolerance, chronic pain, Cockayne Syndrome Type II, Coffin Lowry Syndrome, coma, including persistent vegetative state, complex regional pain syndrome, congenital facial diplegia, congenital myasthenia, congenital myopathy, congenital vascular cavernous malformations, corticobasal degeneration, cranial arteritis, craniosynostosis, Creutzfeldt-Jakob Disease, cumulative trauma disorders, Cushing's Syndrome, cytomegalic inclusion body disease (CIBD), cytomegalovirus infection, dancing eyes-dancing feet syndrome, Dandy-Walker Syndrome, Dawson Disease, De Morsier's Syndrome, Dejerine-Klumpke Palsy, delir in elderly, trauma-induced delir, dementia-multi-infarct, dementia-subcortical, dementia with Lewy Bodies, dermatomyositis, developmental dyspraxia, Devic's Syndrome, diabetic neuropathy, diffuse sclerosis, Dravet's Syndrome, dysautonomia, dysgraphia, dyslexia, dysphagia, dyspraxia, dystonias, early infantile epileptic encephalopathy, Empty Sella Syndrome, encephalitis lethargica, encephalitis and meningitis, encephaloceles, encephalopathy, encephalotrigeminal angiomatosis, epilepsy, Erb's Palsy, Erb-Duchenne and Dejerine-Klumpke Palsies, Fabry's Disease, Fahr's Syndrome, fainting, familial dysautonomia, familial hemangioma, familial idiopathic basal ganglia calcification, familial spastic paralysis, febrile seizures (e.g., GEFS and GEFS plus), Fisher Syndrome, Floppy Infant Syndrome, Friedreich's Ataxia, Gaucher's Disease, Gerstmann's Syndrome, Gerstmann-Straussler-Scheinker Disease, giant cell arteritis, giant cell inclusion disease, globoid cell leukodystrophy, glossopharyngeal neuralgia, Guillain-Barre Syndrome, HTLV-1 associated myelopathy, Hallervorden-Spatz Disease, head injury, headache, hemicrania continua, hemifacial spasm, hemiplegia alterans, hereditary neuropathies, hereditary spastic paraplegia, heredopathia atactica polyneuritiformis, Herpes Zoster Oticus, Herpes Zoster, Hirayama Syndrome, holoprosencephaly, Huntington's Disease, hydranencephaly, hydrocephalus-normal pressure, hydrocephalus, hydromyelia, hypercortisolism, hypersomnia, hypertonia, hypotonia, hypoxia, immune-mediated encephalomyelitis, inclusion body myositis, incontinentia pigmenti, infantile hypotonia, infantile phytanic acid storage disease, infantile refsum disease, infantile spasms, inflammatory myopathy, intestinal lipodystrophy, intracranial cysts, intracranial hypertension, Isaac's Syndrome, Joubert Syndrome, Kearns-Sayre Syndrome, Kennedy's Disease, Kinsbourne syndrome, Kleine-Levin syndrome, Klippel Feil Syndrome, Klippel-Trenaunay Syndrome (KTS), Klüver-Bucy Syndrome, Korsakoff's Amnesic Syndrome, Krabbe Disease, Kugelberg-Welander Disease, kuru, Lambert-Eaton Myasthenic Syndrome, Landau-Kleffner Syndrome, lateral femoral cutaneous nerve entrapment, lateral medullary syndrome, learning disabilities, Leigh's Disease, Lennox-Gastaut Syndrome, Lesch-Nyhan Syndrome, leukodystrophy, Levine-Critchley Syndrome, Lewy Body Dementia, lissencephaly, locked-in syndrome, Lou Gehrig's Disease, lupus-neurological sequelae, Lyme Disease-Neurological Complications, Machado-Joseph Disease, macrencephaly, megalencephaly, Melkersson-Rosenthal Syndrome, meningitis, Menkes Disease, meralgia paresthetica, metachromatic leukodystrophy, microcephaly, migraine, Miller Fisher Syndrome, mini-strokes, mitochondrial myopathies, Mobius Syndrome, monomelic amyotrophy, motor neuron diseases, Moyamoya Disease, mucolipidoses, mucopolysaccharidoses, multi-infarct dementia, multifocal motor neuropathy, multiple sclerosis (MS), multiple systems atrophy (MSA-C and MSA-P), multiple system atrophy with orthostatic hypotension, muscular dystrophy, myasthenia-congenital, myasthenia gravis, myelinoclastic diffuse sclerosis, myoclonic encephalopathy of infants, myoclonus, myopathy-congenital, myopathy-thyrotoxic, myopathy, myotonia congenita, myotonia, narcolepsy, neuroacanthoeytosis, neurodegeneration with brain iron accumulation, neurofibromatosis, neuroleptic malignant syndrome, neurological complications of AIDS, neurological manifestations of Pompe Disease, neuromyelitis optica, neuromyotonia, neuronal ceroid lipofuscinosis, neuronal migration disorders, neuropathy-hereditary, neurosarcoidosis, neurotoxicity, nevus cavernosus, Niemann-Pick Disease, O'Sullivan-McLeod Syndrome, occipital neuralgia, occult spinal dysraphism sequence, Ohtahara Syndrome, olivopontocerebellar atrophy, opsoclonus myoclonus, orthostatic hypotension, Overuse Syndrome, pain-chronic, paraneoplastic syndromes, paresthesia, Parkinson's Disease, parmyotonia congenita, paroxysmal choreoathetosis, paroxysmal hemicrania, Parry-Romberg, Pelizaeus-Merzbacher Disease, Pena Shokeir II Syndrome, perineural cysts, periodic paralyses, peripheral neuropathy, periventricular leukomalacia, persistent vegetative state, pervasive developmental disorders, phytanic acid storage disease, Pick's Disease, Piriformis Syndrome, pituitary tumors, polymyositis, Pompe Disease, porencephaly, Post-Polio Syndrome, postherpetic neuralgia, postinfectious encephalomyelitis, postural hypotension, postural orthostatic tachycardia syndrome, postural tachycardia syndrome, primary lateral sclerosis, prion diseases, progressive hemifacial atrophy, progressive locomotor ataxia, progressive multifocal leukoencephalopathy, progressive sclerosing poliodystrophy, progressive supranuclear palsy, pseudotumor cerebri, pyridoxine dependent and pyridoxine responsive siezure disorders, Ramsay Hunt Syndrome Type I, Ramsay Hunt Syndrome Type II, Rasmussen's Encephalitis and other autoimmune epilepsies, reflex sympathetic dystrophy syndrome, refsum disease-infantile, retsum disease, repetitive motion disorders, repetitive stress injuries, restless legs syndrome, retrovirus-associated myelopathy, Rett Syndrome, Reye's Syndrome, Riley-Day Syndrome, SUNCT headache, sacral nerve root cysts, Saint Vitus Dance, Salivary Gland Disease, Sandhoff Disease, Schilder's Disease, schizencephaly, seizure disorders, septo-optic dysplasia, severe myoclonic epilepsy of infancy (SMEI), shaken baby syndrome, shingles, Shy-Drager Syndrome, Sjogren's Syndrome, sleep apnea, sleeping sickness, Soto's Syndrome, spasticity, spina bifida, spinal cord infarction, spinal cord injury, spinal cord tumors, spinal muscular atrophy, spinocerebellar atrophy, Steele-Richardson-Olszewski Syndrome, Stiff-Person Syndrome, striatonigral degeneration, stroke, Sturge-Weber Syndrome, subacute sclerosing panencephalitis, subcortical arteriosclerotic encephalopathy, Swallowing Disorders, Sydenham Chorea, syncope, syphilitic spinal sclerosis, syringohydromyelia, syringomyelia, systemic lupus erythematosus, Tabes Dorsalis, Tardive Dyskinesia, Tarlov Cysts, Tay-Sachs Disease, temporal arteritis, tethered spinal cord syndrome, Thomson Disease, thoracic outlet syndrome, thyrotoxic myopathy, Tic Douloureux, Todd's Paralysis, Tourette Syndrome, transient ischemic attack, transmissible spongiform encephalopathies, transverse myelitis, traumatic brain injury, tremor, trigeminal neuralgia, tropical spastic paraparesis, tuberous sclerosis, vascular erectile tumor, vasculitis including temporal arteritis, Von Economo's Disease, Von Hippel-Lindau disease (VHL), Von Recklinghausen's Disease, Wallenberg's Syndrome, Werdnig-Hoffinan Disease, Wernicke-Korsakoff Syndrome, West Syndrome, Whipple's Disease, Williams Syndrome, Wilson's Disease, X-Linked Spinal and Bulbar Muscular Atrophy, and Zellweger Syndrome.

Preferred examples of neurodegenerative diseases and neuroinflammatory disorders are selected from the group comprising or consisting of: Alzheimer's disease, Parkinson's disease, Creutzfeldt Jakob disease (CJD), new variant of Creutfeldt Jakobs disease (nvCJD), Hallervorden Spatz disease, Huntington's disease, multisystem atrophy, dementia, frontotemporal dementia, motor neuron disorders of multiple spontaneous or genetic background, amyotrophic lateral sclerosis (ALS), spinal muscular atrophy, spinocerebellar atrophies (SCAs), schizophrenia, affective disorders, major depression, meningoencephalitis, bacterial meningoencephalitis, viral meningoencephalitis, CNS autoimmune disorders, multiple sclerosis (MS), acute ischemic/hypoxic lesions, stroke, CNS and spinal cord trauma, head and spinal trauma, brain traumatic injuries, arteriosclerosis, atherosclerosis, microangiopathic dementia, Binswanger' disease (Leukoaraiosis), cochlear degeneration, cochlear deafness, AIDS-related dementia, fragile X-associated tremor/ataxia syndrome (FXTAS), progressive supranuclear palsy (PSP), striatonigral degeneration (SND), olivopontocerebellar degeneration (OPCD), Shy Drager syndrome (SDS), age dependant memory deficits, neurodevelopmental disorders associated with dementia, Down's Syndrome, synucleinopathies, superoxide dismutase mutations, trinucleotide repeat disorders as Huntington's Disease, trauma, hypoxia, vascular diseases, vascular inflammations, CNS-ageing. Also age dependant decrease of stem cell renewal may be addressed.

Particularly preferred examples of neurodegenerative diseases and neuroinflammatory disorders are selected from the group comprising or consisting of: Alzheimer's disease, Parkinson's disease, Huntington's disease, amyotrophic lateral sclerosis (ALS), hydrocephalus, CNS and spinal cord trauma such as spinal cord injury, head and spinal trauma, brain traumatic injuries, cochlear deafness, AIDS-related dementia, trinucleotide repeat disorders as Huntington's Disease, and CNS-aging.

The words "treatment", "treating" and variations thereof refer to curing, mitigating or relieving symptoms of a disease, medical condition or injury.

Transmucosal delivery refers to transport of an active agent across a mucous membrane, such as buccal delivery (via the mucosa on the inside lining of the cheeks), sublingual delivery (via the mucosa at the floor of the mouth, i.e., under the tongue), and palatal delivery (via mucosa at the roof of the mouth). However, other, non-oral transmucosal delivery techniques may be used, such as via nasal, vaginal, rectal or ocular routes. Enteral delivery refers to passing the active agent through the gastrointestinal tract, either naturally via the mouth and esophagus, or through an artificial opening (e.g., stoma) and absorbing the active agent in the intestine.

Leukotriene receptor antagonists include, but are not necessarily limited to, Montelukast and zafirlukast. Active agents capable of existing in various forms, such as salts, esters, prodrugs, etc., are, unless otherwise indicated, encompassed by reference to the base drug. For example, the term "Montelukast" is intended to encompass all forms, including salts (e.g., Montelukast sodium), esters and prodrugs.

Leukotriene synthesis inhibitors include, but are not necessarily limited to, zileuton.

A film layer is a sheet-like material having a thickness that is much less than its length or width. For example, oral transmucosal devices typically have a thickness on the order of about 100 µm to 500 µm (i.e., 0.1 mm to 0.5 mm), although thicker or thin films may be suitable; and width and length dimensions typically on the order of about 5 mm to 36 mm, although larger or smaller dimensions can be used.

The film dosage form can comprise a single film layer, or multiple layers. For example, in the case of buccal or sublingual film dosage forms, it can be beneficial to employ a biocompatible layer (e.g., a bioadhesive layer) containing the active agent and a non-adhesive barrier layer to prevent or reduce ingestion of the active agent(s) and ensure that all or most of the active agent crosses the mucous membrane to which the bioadhesive layer is applied. The term "bioadhesive" means that the composition of the film layer is formulated to adhere to the selected mucous membrane through which delivery of the active agent is targeted, and encompasses the term "mucoadhesive.". For example, bioadhesive polymers used in formulating the film should be selected to exhibit adequate adhesion within the environment at the targeted mucous membrane to ensure that the bioadhesive layer remains in contact with the mucous membrane to which it is applied and allows the active agent to directly enter the blood stream through the mucous membrane.

A safe and effective amount generally refers to an amount that provides a beneficial or therapeutic effect, i.e., provides a curing or mitigating effect on disease or disease symptoms, but which is sufficiently low to avoid severe or life-threatening side effects when the active agent is administered and delivered transmucosally and/or enterally.

Preferred film dosage forms include sublingual and buccal film oral dosage forms. Buccal and/or sublingual mucosa absorption allows the drug to be absorbed directly into the blood stream skipping the hepatic metabolism. From a pharmaceutical formulation perspective this is particularly challenging, as the process of transmucosal permeation needs to be carefully optimized to obtain an acceptable pharmacokinetic profile. MTL is more soluble in its deprotonated state under basic pH environment. Therefore, electrostatic complexation with a cationic biopolymer can be used under these conditions to further improve MTL solubility and membrane permeation. The use of a rapidly wetting, dissolving film matrix will also improve the dissolution profile of the API and consequently improve bioavailability. The convenience of an oral film over tablets allows better patient compliance, as many individuals have difficulty swallowing or might not have water readily available.

Leukotriene blockers (i.e., leukotriene receptor antagonists and leukotriene synthesis inhibitors) can function to improve cognitive impairment by reducing the neuroinflammatory response within the brain. Leukotriene blockers, such as MTL, must therefore cross the blood-brain barrier and accumulate in the CSF. Consequently during our clinical trials, patterns were tested for CSF levels of MTL after 3 and 7 hours respectively, (see Table 1). What is most surprising about this finding is that between the 3 and 7 hour test points, the concentration of MTL continued to increase. This is particularly unexpected as the plasma levels show a Tmax value between 2-4 hours only, indicating that the maximum accumulated concentration is rapidly reached in the blood. As only two data points were taken during our clinical study it remains unclear if the time point at 7 hours represents the Cmax, or if the Cmax occurs after 7 hours as more MTL accumulates but is cleared at a much slower rate. This is of great significance when compared to the known treatments, wherein a strict regimen of continuous dosing was required to maintain effective levels of MTL for cognitive improvement. Our data clearly demonstrates that regular dosing every 2 hours is not necessary to maintain effective levels of MTL in the CSF.

TABLE 1

Pharmacokinetic Data for CSF Concentrations

| Sample | Concentration at 3 hours (ng/ml) | Concentration at 7 hours (ng/ml) |
|---|---|---|
| Intelgenx MTL Film | 3.60 | 4.20 |

We have performed a clinical study of our product to determine the pharmacokinetics of the API loaded into this pharmaceutical platform. Our film product and the Singulair® product both contain 10 mg MTL free base. Singulair® is the marketed formulation of MTL, commonly prescribed for asthma sufferers. It consists of a 10 mg loaded API tablet. The Cmax and Tmax values are listed below, see Table 2. Results indicate that we have approximately 1.5 times the Cmax and AUC values compared to the Singulair® reference. These higher values for our films means that we could load less API into the film product and achieve the same Cmax/AUC as the Singulair® reference product.

TABLE 2

Pharmacokinetic Data for Plasma Concentrations

| Sample | Cmax (ng/ml) | Tmax (hrs) | AUC |
|---|---|---|---|
| Intelgenx MTL Film | 599 | 2.70 | 3910 |
| Singulair ® product | 386 | 3.63 | 2617 |

The active agent can be combined or blended with film forming polymers and/or bioadhesive polymers to obtain a balanced combination of properties suitable for an oral or other transmucosal delivery device. Examples of suitable film forming polymers exhibiting bioadhesion include hydroxypropyl cellulose, hydroxymethylcellulose, natural or synthetic gum, polyvinyl alcohol, polyethylene oxide, homo- and copolymers of acrylic acid crosslinked with a polyalkenyl polyether or divinyl alcohol, polyvinylpyrrolidone, hydroxypropylmethyl cellulose, sodium alginate, pectin, gelatin and maltodextrins. In certain embodiments or aspects of this disclosure, the active agent can be combined with film forming neutral polysaccharides such as pullulan.

In order to inhibit ionization of the active agent after administration (i.e., application to oral mucosa) and during transmucosal delivery of the active agent, the bioadhesive film can further comprise an acidifying agent in an amount that is sufficient to adjust the local pH in the bioadhesive layer, after it has been adhered to oral mucosa and imbibed with saliva, to a value of from about 6 to about 3. Acidifying agents that are pharmaceutically acceptable include 1-hydroxy-2-naphthoic acid, 2,2-dichloroacetic acid, 2-hydroxyethanesulfonic acid, 2-oxoglutaric acid, 4-acetamidobenzoic acid, 4-aminosalicylic acid, acetic acid, adipic acid, ascorbic acid (L), aspartic acid (L), benzenesulfonic acid, benzoic acid, camphoric acid (+), camphor-10-sulfonic acid (+), capric acid (decanoic acid), caproic acid (hexanoic acid), caprylic acid (octanoic acid), carbonic acid, cinnamic acid, citric acid, cyclamic acid, dodecylsulfuric acid, ethane-1,2-disulfonic acid, ethanesulfonic acid, formic acid, fumaric acid, galaclaric acid, gentisic acid, glucoheptonic acid (D), gluconic acid (D), glucuronic acid (D), glutamic acid, glutaric acid, glycerophosphoric acid, glycolic acid, hippuric acid, hydrobromic acid, hydrochloric acid, isobutyric acid, lactic acid (DL), lactobionic acid, lauric acid, maleic acid, malic acid (–L), malonic acid, mandelic acid (DL), methanesulfonic acid, naphthalene-1,5-disulfonic acid, naphthalene-2-sulfonic acid, nicotinic acid, nitric acid, oleic acid, oxalic acid, palmitic acid, pamoic acid, phosphoric acid, proprionic acid, pyroglutamic acid (–L), salicylic acid, sebacic acid, stearic acid, succinic acid, sulfuric acid, tartaric acid (+L), thiocyanic acid, toluenesulfonic acid (p), and undecylenic acid.

Penetration enhancing agents can also or alternatively be employed to further increase the rate and/or total amount of absorption of the active agent. Examples of penetration enhancers that can be advantageously employed include 2,3-lauryl ether, phosphatidylcholine, aprotinin, polyoxyethylene, azone, polysorbate 80, benzalkonium chloride, polyoxyethylene, cetylpyridinium chloride, phosphatidylcholine, cetyltrimethyl ammonium bromide, sodium EDTA, cyclodextrin, sodium glycocholate, dextran sulfate 16 sodium glycodeoxycholate. Other penetration enhancers include surfactants, bile salts (by extracting membrane protein or lipids, by membrane fluidization, by producing reverse micellization in the membrane and creating aqueous channels), fatty acids (that act by disrupting intercellular lipid packing), azone (by creating a region of fluidity in intercellular lipids), pore forming agents (e.g., molecules or particles that insert into the lipid membrane creating a hole through which the API can pass) and alcohols (by reorganizing the lipid domains and by changing protein conformation).

Examples of surfactants that can be employed to enhance penetration and/or wettability of the film to promote adhesion, include polysorbates (Tween™), sodium dodecyl sulfate (sodium lauryl sulfate), lauryl dimethyl amine oxide, cetyltrimethylammonium bromide (CTAB), polyethoxylated alcohols, polyoxyethylene sorbitan octoxynol (Triton X100™), N,N-dimethyldodecylamine-N-oxide, hexadecyltrimethylammonium bromide (HTAB), polyoxyl 10 lauryl ether, Brij 721™, bile salts (sodium deoxycholate, sodium cholate) polyoxyl castor oil (Cremophor™), nonylphenol ethoxylate (Tergitol™), cyclodextrins, lecithin, methylbenzethonium chloride (Hyamine™).

The solubility and disintegration profiles of the film can influence the bioavailability of the drug. Therefore, certain embodiments of the film platform will contain specific quantities of disintegrants to control the residence time of the film in the oral cavity. Certain forms of the drug product may contain between 0-10% by mass of a disintegrant. Examples of disintegrants that could be used are Maltodextrin, Citric acid, Sodium starch, glycolate, crosslinked polyvinylpyrrolidone (crospovidone), crosslinked sodium carboxymethyl cellulose, Calcium silicate, Alginic acid, and vinylpyrrolidone-vinyl acetate copolymers.

Stability enhancing agents can be added to the film to prevent photodegradation, oxidation, and/or microbial contamination. Photodegradation inhibitors include ultraviolet radiation absorbers and pigments. Ultraviolet absorbers include hydroxyl benzophenones and hydroxyphenyl benzotriazoles. Pigments that can be added to the film include various metal oxides, such as titanium dioxide ($TiO_2$), ferric oxide ($Fe_2O_3$), iron oxide ($Fe_3O_4$), and zinc oxide ($ZnO$).

Other additives, such as excipients or adjuvants, that can be incorporated into the film include flavors, sweeteners, coloring agents (e.g., dyes), plasticizers, and other conventional additives that do not deleteriously affect transmucosal delivery of the active agent, oral mucoadhesivity, or their important film properties.

The film can be used in a monolayer form, or in a multilayer form. In particular, a barrier layer can be advantageously employed to prevent the active agent from diffusing through a bioadhesive film into the oral cavity of a subject after it is adhered to the subject's oral mucosa. The barrier layer is preferably comprised of polymers having a low solubility in water. A combination of water-insoluble polymer(s) and a minor amount of a water-soluble polymer(s) can be employed to maintain a barrier that prevents loss of the active agent to the oral cavity until an effective or desired amount of the active agent has been transmucosally delivered, and which allows erosion and/or dissolution thereafter. In some cases it may be advantageous to employ, in the barrier layer, higher molecular weight polymer analogs of the polymer(s) used in the bioadhesive layer. The higher molecular weight (for, equivalently, higher viscosity) analogs are typically more resistant to diffusion and dissolution, and exhibit better compatibility than if polymers of a different chemical type are used.

Examples of water-insoluble polymers that can be employed in the barrier layer include polysiloxanes (silicone polymers), ethyl cellulose, propyl cellulose, polyethylene, and polypropylene. One or more of these polymers may comprise a majority of the barrier film layer by weight (i.e., at least 50 percent). Water soluble hydroxypropyl cellulose can be used in a minor amount to facilitate erosion and/or dissolution of the barrier layer after it has served its function during transmucosal delivery of the active agent. High viscosity polymer could also be used to create a barrier and limit erosion. For example, hydroxypropyl cellulose, polyethylene oxide, polyvinyl pyrrolidone and any other polymer soluble in water, but exhibiting high viscosity, can be used.

The active agent, in certain embodiments, can be optionally combined with a polymer capable of interacting with the active agent, and exhibiting mucoadhesivity in the oral cavity of a subject, and/or compatible and combinable with oral mucoadhesive materials to facilitate adhesion to oral mucosal tissue (e.g., buccal and labial mucosa). Examples of polymers that exhibit bioadhesion in the oral cavity include chitosan (and/or other glucosamine and acetylglucosamine polymers), poly(amino acids), dextran, galactomannan polymers (tara gum), cellulose, and cyclodextrin and/or their derivates and copolymer analogs. Such materials are commercially available, and/or have been thoroughly described in the open literature. Other polymers and copolymers that may be used include polyethylene imine, poly-L-lysine, poly(amidoamine)s, poly(ammo-co-ester)s, and poly(2-N-N-dimethylaminoethylmethacrylate), and their copolymer analogs, all of which are thoroughly described in the open literature.

A preferred amount of Montelukast sodium per unit dosage form is from about 0.5 mg to 20 mg, 1 mg to 20 mg, or 5 mg to 10 mg.

Illustrative, but non-limiting, examples of a formulations used to prepare a MTL Na are shown in Tables 3-9.

TABLE 3

| Item # | Description | Function | Composition (% wet (w/w) |
|---|---|---|---|
| A | Methanol | Solvent (will be removed during manufacturing) | 0.29 |
| B | Purified Water | Solvent (will be removed during manufacturing) | 79.68 |
| 1 | Starch | Filler | 1.81 |
| 2 | HPC SL | Film former polymer | 8.37 |
| 3 | Xanthan gum | Thickener | 0.88 |
| 4 | Sucralose | Sweetener | 0.44 |
| 5 | Glycerol | Plasticizer | 1.85 |
| 6 | Montelukast Sodium | Active | 3.3 |
| 7 | Ascorbic acid | Stabilizer | 0.01 |
| 8 | Methylparaben | Anti-microbial agent | 0.11 |
| 9 | Titanium Dioxide | Opacifier | 0.27 |
| 10 | Yellow #10 | Color | 0.28 |
| 11 | HPC LF | Film former polymer | 0.73 |
| 12 | Calcium Carbonate | pH Modifier | 0.51 |
| 13 | Sodium glycocholate | Permeation Enhancer | 1.47 |
| Total | | | 100 |

TABLE 4

| Item # | Description | Function | Composition (% wet (w/w) |
|---|---|---|---|
| A | Methanol | Solvent (will be removed during manufacturing) | 0.2 |
| B | Purified Water | Solvent (will be removed during manufacturing) | 79.68 |
| 1 | Povidone | Film former polymer | 11.08 |
| 2 | Locust Bean Gum | Thickener | 0.88 |
| 3 | PEG 300 | Plasticizer | 0.15 |
| 4 | Labrafil M1944CS | Permeation Enhancer | 0.89 |
| 5 | Sucralose | Sweetener | 0.44 |
| 6 | Citric Acid | pH Modifier | 0.61 |
| 7 | Montelukast Sodium | Active | 3.3 |
| 8 | Sodium Edatate | Stabilizer | 0.01 |
| 9 | Propylparaben | Anti-microbial agent | 0.1 |
| 10 | Titanium Dioxide | Opacifier | 0.27 |
| 11 | Yellow #10 | Color | 0.28 |
| 12 | HPC-GXF | Film former polymer | 2.11 |
| Total | | | 100 |

TABLE 5

| Item # | Description | Function | Composition (% wet (w/w) |
|---|---|---|---|
| A | Methanol | Solvent (will be removed during manufacturing) | 0.29 |
| B | Purified Water | Solvent (will be removed during manufacturing) | 79.68 |
| 1 | Starch | Filler | 1.81 |
| 2 | Pullulan | Film former polymer | 8.37 |
| 3 | Tara gum | Viscosity Modifier | 0.88 |
| 4 | PEG 300 | Plasticizer | 0.15 |
| 5 | Sorbitol P60W | Plasticizer | 1.83 |
| 6 | Sucralose | Sweetener | 0.44 |
| 7 | Glycerol | Plasticizer | 1.85 |
| 8 | Montelukast Sodium | Active | 3.30 |
| 9 | BHT | Stabilizer | 0.01 |
| 10 | Propylparaben | Anti-microbial agent | 0.11 |
| 11 | Titanium Dioxide | Opacifier | 0.27 |
| 12 | Yellow #10 | Color | 0.28 |
| 13 | HPC LF | Film former polymer | 0.73 |
| Total | | | 100 |

TABLE 6

| Item # | Description | Function | Composition (% wet (w/w) |
|---|---|---|---|
| A | Methanol | Solvent (will be removed during manufacturing) | 0.29 |
| B | Purified Water | Solvent (will be removed during manufacturing) | 79.68 |
| 1 | Starch | Filler | 0.74 |
| 2 | PEO 200K | Film former polymer | 8.37 |
| 3 | PEO 100K | Film former polymer | 2.35 |
| 4 | Menthol | Flavor | 1.3 |
| 5 | Sorbitol P60W | Plasticizer | 1.68 |
| 6 | Sucralose | Sweetener | 0.44 |
| 7 | Citric Acid | pH Modifier | 0.45 |
| 8 | Montelukast Sodium | Active | 3.3 |
| 9 | Sodium Sulfite | Stabilizer | 0.01 |
| 10 | Methylparaben | Anti-microbial agent | 0.11 |
| 11 | Titanium Dioxide | Opacifier | 0.27 |
| 12 | Yellow #10 | Color | 0.28 |
| 13 | HPC JF | Film former polymer | 0.73 |
| Total | | | 100 |

TABLE 7

| Item # | Description | Function | Composition (% wet (w/w) |
|---|---|---|---|
| A | Methanol | Solvent (will be removed during manufacturing) | 0.29 |
| B | Purified Water | Solvent (will be removed during manufacturing) | 78.66 |
| 1 | Sodium Hydroxide | pH Modifier | 0.65 |
| 2 | HPMC E5 | Film former polymer | 3.21 |
| 3 | HPC-L | Film former polymer | 9.63 |
| 4 | PEG 300 | Plasticizer | 0.15 |
| 5 | Sorbitol P60W | Plasticizer | 1.83 |
| 6 | Sucralose | Sweetener | 0.44 |
| 7 | Sodium Metabisulfite | Stabilizer | 0.59 |
| 8 | Montelukast Sodium | Active | 3.3 |
| 9 | Sodium Edetate | Stabilizer | 0.01 |
| 10 | Propylparaben | Anti-microbial agent | 0.11 |
| 11 | Yellow #10 | Color | 0.28 |
| 12 | Oleic acid | Permeation Enhancer | 0.85 |
| Total | | | 100.00 |

TABLE 8

| Item # | Description | Function | Composition (% wet (w/w) |
|---|---|---|---|
| A | Methanol | Solvent (will be removed during manufacturing) | 0.29 |
| B | Purified Water | Solvent (will be removed during manufacturing) | 79.68 |
| 1 | Sodium Hydroxide | pH Modifier | 0.84 |
| 2 | Pullulan | Film former polymer | 9.34 |
| 3 | Xanthan gum | Thickener | 1.88 |
| 4 | PEG 300 | Plasticizer | 0.15 |
| 5 | Sodium sulfite | Stabilizer | 0.65 |
| 6 | Sucralose | Sweetener | 0.44 |
| 7 | Glycerol | Plasticizer | 1.85 |
| 8 | Montelukast Sodium | Active | 3.3 |
| 9 | Azone | Permeation Enhancer | 0.92 |
| 10 | Propylparaben | Anti-microbial agent | 0.11 |
| 11 | Titanium Dioxide | Opacifier | 0.27 |
| 12 | Yellow #10 | Color | 0.28 |
| Total | | | 100.00 |

TABLE 9

| Item # | Description | Function | Composition (% wet (w/w) |
|---|---|---|---|
| A | Methanol | Solvent (will be removed during manufacturing) | 0.29 |
| B | Purified Water | Solvent (will be removed during manufacturing) | 79.68 |
| 1 | Ascorbic acid | Stabilizer | 0.97 |
| 2 | HPC-SL | Film former polymer | 9.66 |
| 3 | Xanthan gum | Thickener | 1.43 |
| 4 | PEG 300 | Plasticizer | 0.15 |
| 5 | Sorbitol P60W | Plasticizer | 1.83 |
| 6 | Sucralose | Sweetener | 0.44 |
| 7 | Labrafil M1944CS | Permeation Enhancer | 1.02 |
| 8 | Montelukast Sodium | Active | 3.3 |
| 9 | Sodium metabisulfite | Stabilizer | 0.84 |
| 10 | Propylparaben | Anti-microbial agent | 0.11 |
| 11 | Yellow #10 | Color | 0.28 |
| Total | | | 100.00 |

Preparation of a film product typically involves casting or otherwise thinly spreading the liquid film formulation on a substrate, drying (e.g., evaporating) all or most of the solvent(s) from the film to produce a thin, solid film sheet of material, and cutting the solid film sheet into individual unit dosage forms.

The above description is considered that of the preferred embodiment(s) only. Modifications of these embodiments will occur to those skilled in the art and to those who make or use the illustrated embodiments. Therefore, it is understood that the embodiment(s) described above are merely exemplary and not intended to limit the scope of this disclosure, which is defined by the following claims as interpreted according to the principles of patent law, including the doctrine of equivalents.

The invention claimed is:

1. A film dosage form for administration in the buccal cavity, comprising:
   a bioadhesive film layer comprising polymers selected to exhibit adhesion to a mucous membrane at the buccal cavity;
   a safe and effective amount of a leukotriene blocker incorporated into the film layer; and
   the film dosage form providing increased maximum plasma concentration in a human as compared with a tablet having identical loading of the leukotriene blocker, wherein the leukotriene blocker is Montelukast, wherein the safe and effective amount of Montelukast is between 0.5 mg to 20 mg;

the bioadhesive film layer further comprising a plurality of plasticizers, including polyethylene glycol, sorbitol and glycerol, wherein the amount of sorbitol is greater than the amount of polyethylene glycol, and wherein the amount of glycerol is greater than the amount of polyethylene glycol.

2. The film dosage form of claim 1, wherein the safe and effective amount of Montelukast is 10 mg.

3. A film dosage form for administration in the buccal cavity, comprising:

a bioadhesive film layer comprising polymers selected to exhibit adhesion to a mucous membrane at the buccal cavity:

a safe and effective amount of a leukotriene blocker incorporated into the film layer;

the film dosage form providing increased plasma concentration in a human as compared with an immediate release oral tablet having identical loading of the leukotriene blocker, wherein the leukotriene blocker is Montelukast, wherein the safe and effective amount of Montelukast is between 0.5 mg to 20 mg;

the bioadhesive film layer further comprising a plurality of plasticizers, including polyethylene glycol, sorbitol and glycerol, wherein the amount of sorbitol is greater than the amount of polyethylene glycol, and wherein the amount of glycerol is greater than the amount of polyethylene glycol.

* * * * *

UNITED STATES PATENT AND TRADEMARK OFFICE
CERTIFICATE OF CORRECTION

PATENT NO. : 9,949,934 B1
APPLICATION NO. : 15/299054
DATED : April 24, 2018
INVENTOR(S) : Horst Zerbe et al.

It is certified that error appears in the above-identified patent and that said Letters Patent is hereby corrected as shown below:

In the Claims

Column 12, Line 65 (Claim 1) "and" should be deleted.

Signed and Sealed this
Nineteenth Day of June, 2018

Andrei Iancu
*Director of the United States Patent and Trademark Office*